United States Patent
Kim et al.

(10) Patent No.: US 6,706,917 B1
(45) Date of Patent: Mar. 16, 2004

(54) PREPARING METHOD OF 2-PHENYLALKANOIC ACID DERIVATIVES

(75) Inventors: Dae Whang Kim, Daejeon (KR); Hae Sung Chang, Daejeon (KR); Young Kwan Ko, Daejeon (KR); Jae Wook Ryu, Daejeon (KR); Jae Chun Woo, Daejeon (KR); Dong Wan Koo, Daejeon (KR)

(73) Assignee: Korea Research Institute of Chemical Technology (KR)

( * ) Notice: Subject to any disclaimer, the term of this patent is extended or adjusted under 35 U.S.C. 154(b) by 0 days.

(21) Appl. No.: 10/169,505

(22) PCT Filed: Jan. 4, 2000

(86) PCT No.: PCT/KR00/00003

§ 371 (c)(1),
(2), (4) Date: Jul. 3, 2002

(87) PCT Pub. No.: WO01/49648

PCT Pub. Date: Jul. 12, 2001

(51) Int. Cl.⁷ .................. C07C 65/00; C07C 381/00; C07D 307/78
(52) U.S. Cl. .............. 562/405; 562/426; 549/468
(58) Field of Search ................. 562/405, 426; 549/468

(56) References Cited

PUBLICATIONS

Baiocchi et al., Aromatization of Aliphatic Compounds, 1979, p. 434.*

* cited by examiner

*Primary Examiner*—Alan L. Rotman
*Assistant Examiner*—Taylor V. Oh
(74) *Attorney, Agent, or Firm*—Finnegan, Henderson, Farabow, Garrett & Dunner, LLP

(57) ABSTRACT

The present invention relates to a preparing method of 2-phenylalkanoic acid derivatives and more particluarly, to the preparing method of 2-phenylalkanoic acid derivatives expressed by formula (1) from 5,6-dihydro-2(4H)-benzofuranone as a starting material in the presence of a catalyst, organic acid alkali metal salt, in a mild condition, wherein $R_1$ prepresents benzoyl, naphthoyl, nicotinoyl, furoyl or thenoyl group; and $R_2$ prepresents a hydrogen atom or $C_1$–$C_6$ alkyl group.

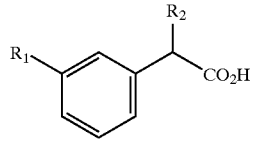

(1)

6 Claims, No Drawings

PREPARING METHOD OF 2-PHENYLALKANOIC ACID DERIVATIVES

BACKGROUND OF THE INVENTION

Field of the Invention

The present invention relates to a preparing method of 2-phenylalkanoic acid derivatives and more particularly, to the preparing method of 2-phenylalkanoic acid derivatives expressed by formula 1 from 5,6-dlihydro-2(4H)-benzofuranoneas a starting material in the presence of a catalyst, organic acid alkali metal salt, in a mild condition,

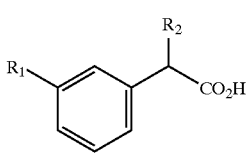
(1)

wherein $R_1$ represents benzoyl, naphthoyl, nicotinoyl, furoyl or thenoyl group; and $R_2$ represents a hydrogen atom or $C_1$~$C_6$ alkyl group.

2-Phenylalkanoic acid derivatives expressed by formula 1 is widely known and used as pharmaceutical drugs as well as a major intermediate for the synthesis of various pharmaceutical drugs [*Brit. Med. J.* 1992, 4, 398].

Also, the preparing methods of 2-Phenylalkanoic acid derivatives expressed by formula 1 have being developed extensively and some representative examples are disclosed in DE 2,624,174, *Tetralzedron Lett.* 1979, 46, 4499 and *Synthwesis*, 1979, 434. In conventional preparing methods, the reactions are performed in the presence of excess pyridinium hydrogen chloride salt as in the following scheme 1, Scheme 1

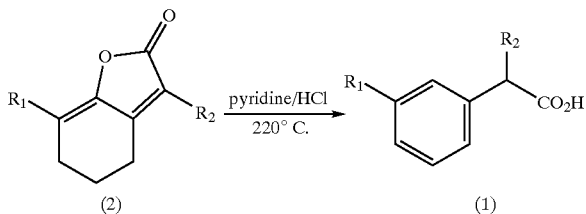

wherein $R_1$ and $R_2$ are the same as explained above.

However, the above conventional preparing methods are undesirable in requirement of extra controlling system for corrosion in chemical plants due to use of excess amount of pyridinium hydrochloric acid salt (about 11 equivalents excess) possessing strong corrosion with heating at 230° C. On top of that, these methods are economnically unfavorable for excess use of expensive pyridinium hydrochloric acid salt and industrially unfavorable for requirement of special carefulness to carry pyridinium hydrochloric acid salt due to its powerful hygroscopicity. When pyridinium hydrochloric acid salt is used less than 1 equivalent, the reactivity is too low to use for industrial purpose. Using of pyridinium hydrochloric acid salt can be also dangerous by blocking a condenser when it gets cool down by turning to solid due to its sublimation property at high temperature.

SUMMARY OF THE INVENTION

The inventors made extensive efforts to solve the problems of the conventional preparing methods. As a result, it was realized that the use of organic acid alkali metal salt instead of expensive pyridinium hydrocliloric acid salt as a reaction catalyst could solve all the said problems.

Thus, an object of the present invention is to provide an industrially advantageous preparing method of 2-phenylalkanoic acid derivatives from 5,6-dihydro-2(4H)-benzofuranone in the presence of alkali catalyst, organic acid alkali metal salt.

Detailed Description of the Invention

The present invention is characterized by a preparing method of 2-phenylalkanoic acid derivatives expressed by formula 1, wherein the starting material, 5,6-dihydro-2(4H)-benzofuranone, expressed by formula 2 is reacted with organic acid alkali metal salt as a catalyst,

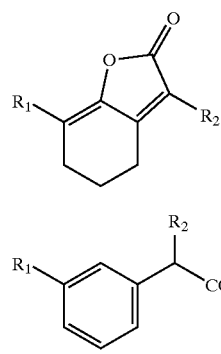
(2)

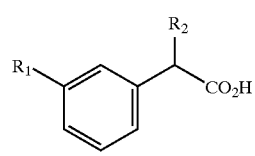
(1)

wherein $R_1$ represents benzoyl, naphthoyl, nicotinoyl, furoyl or thenoyl group; and $R_2$ represents a hydrogen atom or $C_1$~$C_6$ alkyl group.

The Detailed description of the present invention is given hereunder.

The most characteristic of the present invention is a selection of organic acid alkali metal salt as a catalyst in the preparing method.

Organic acid alkali metal salt as a catalyst of the present invention can be used for industrial purpose due to its relatively cheap price without corrosion of machineries, thus making it favorable economically by using catalytic amount to provide sufficient effects. Organic acid alkali metal salt does not react with moisture in air, thus it is easy to handle.

Organic acid alkali metal salts having superiority mentioned above are salts of 2-phenylalkanoic acid derivatives expressed by formula 1 or salts expressed by formula 3, $$R—CO_2^-M^+ \quad (3)$$

wherein R represents a hydrogen atom, $C_1$~$C_{13}$ alkyl, $C_1$~$C_{13}$ haloalkyl, $C_1$~$C_{13}$ alkenyl, $C_1$~$C_{13}$ alkinyl, $C_1$~$C_{13}$alkoxyalkyl, $C_1$~$C_{13}$ cycloalkyl, or A-$(CH_2)_n$, wherein A is aryl which is phenyl, naphthyl, pyridyl, quinolyl and thiophenyl, the aryl having more than one of the group consisting of a hydrogen atom and functional groups halogen atom, $C_1$~$C_3$ alkyl, $C_1$~$C_3$ alkoxy and nitro group, and n is 0 or an integer of 1~4and M represents an alkali metal atom. An alkyl group of the present invention includes straight or branched alkyl group.

Organic acid alkali metal salt used as a catalyst in the present invention includes all of the alkali metal compounds forming $RCO_2M$ expressed by, formula 3 in the reaction. This reaction catalyst can be used alone or as a mixture. It is preferable to use organic acid potassium salt or organic acid sodium salt as an organic acid alkali metal salt expressed by formula 3. Organic acid alkali metal salt is used preferably in the range of 0.01 to 5 molar equivalents to the starting material expressed by formula 2. Even though organic acid alkali metal salt can be used more than 5 molar equivalents without harming a reaction, it is not favorable economically.

Aromatization of 5,6-dihydro-2(4H)-benzofuranone expressed by formula 2 is performed without any solvent or with a little amount of solvent, if necessary, at 150~250° C. preferably.

5,6-Dihydro-2(4H)-benzofuranone expressed by formula 2,used as a starting material of the present invention, are well known compounds and prepared easily using known preparing methods (DE Patent 2,624,174, *Tetraliedron Lett.* 1979, 46, 4499,*Syntlhesis*, 1979, 434).

The preparing method described in the present invention resolves problems caused by using pyridinium hydrochloric acid salt and provides superior result in reaction rate and yield by using organic acid alkali metal salt.

The following examples are intended to be illustrative of the present invention and should not be construed as limiting the scope of this invention defined by the appended claims.

Example 1

Preparation of α-Methyl-3-(2-thenoyl)benzene Acetic Acid

A mixture of 7-(2-tenoyl)-3-methyl-5,6-dihydro-2(4H)-benzofuranone (10 g) and acetic acid potassium salt (0.3 g) was added to a reactor and stirred for 3 hr at 220° C. The reaction mixture was cooled down to room temperature. Toluene and water were added to the reaction mixture and acidified to pH 2 with 5% hydrochloric acid. Toluene layer separated was dried over anhydrous $MgSO_4$,filtered and evaporated to give crude product. The crude product was purified by column chromatograph on silica gel by eluting with a mixture of ethylacetate and n-hexane, (1:5) to give the desired product (9.13 g, 91%).

$^1$H NMR ($CDCl_3$): δ 1.43 (d, 3H), 3.82 (q, 1H), 7.12 (m, 1H), 7.41~7.82 (m, 6H).

Example 2

Preparation of α-Methyl-3(2-naphthoyl)benzene Acetic Acid

A mixture of 7-(2-naphthoyl)-3-methyl-5,6-dihydro-2(4H)-benzofuranone (10 g) and acetic acid potassium salt (0.3 g) was added to a reactor and stirred for 1 hr at 220° C. The reaction mixture was cooled down to room temperature. Toluene and water were added to the reaction mixture and acidified to pH 2 with 5% hydrochloric acid. Toluene layer separated was dried over anhydrous $MgSO_4$, filtered and evaporated to give crude product. The crude product was purified by column chromatograph on silica gel by eluting with a mixture of ethylacetate and n-hexane (1:5) to give the desired product (9:42 g, 94 % .

$^1$H NMR ($CDCl_3$): δ 1.56 (d, 3H), 3.84 (q, 1H), 7.43~8.25 (m, 11H).

Example 3:

Preparation of 2-(3Benzolyphenyl)-propionic Acid

A mixture of 7-benzolyl-3-methyl-5,6-dihydro-2(4H)-benzofuranone, (10 g) and a catalyst represented in the following table 1 was added to a reactor. The reaction mixture was cooled down to room temperature. Toluene and water were added to the reaction mixture and acidified to pH 2 with 5% hydrochloric acid. Toluene layer separated was dried over anhydrous $MgSO_4$, filtered and evaporated to give crude product. The crude product was purified by column chromatograph on silica gel by eluting with a mixture of erhylacetate and n-hexane (1:5) to give the desired product as white crystal.

m.p.:93~95° C.; $^1$H NMR ($CDCl_3$): δ 1.52 (d, 3H, $CH_3$), 3.78(q, 1H, CHCOOH), 7.3~7.81 (m, 9H, Ar-H), 11.6 (brs, 1H, COOH).

TABLE 1

| Catalyst | | | | |
|---|---|---|---|---|
| Type | Amount (eq.) | Temperature (° C.) | Reaction Time (hr) | Yield (%) |
| $HCO_2^-Na^+$ | 0.2 | 225 | 2.5 | 86 |
| $CH_3CO_2^-K^+$ | 0.025 | 225 | 2 | 95 |
| | 0.07 | 230 | 3 | 97 |
| | 0.38 | 195 | 4 | 94 |
| | 0.5 | 170 | 11 | 93 |
| $CH_3CH_2CO_2^-Na^+$ | 0.08 | 225 | 3 | 91 |
| | 0.5 | 195 | 6 | 90 |
| $FCH_2CO_2^-Na^+$ | 0.2 | 225 | 2.5 | 61 |
| $CH_3-(CH_2)_3-\underset{\underset{C_2H_5}{\mid}}{CH}-CO_2^-Na^+$ | 0.3 | 195 | 6 | 91 |

TABLE 1-continued

| Catalyst | | | | |
|---|---|---|---|---|
| Type | Amount (eq.) | Temperature (° C.) | Reaction Time (hr) | Yield (%) |
| ![phenyl-CO2Na] | 0.36 | 225 | 12 | 84 |
| ![benzoyl-phenyl-CH(CH3)COOK] | 0.2 | 225 | 3 | 91 |
| Pyridinium hydrochloric acid salt | 0.07 | 230 | 3 | 20 |
| | 11 | 230 | 5 | 80 |

As described above, the present invention provides an industrially advantageous preparing method of 2-phenylalkanoic acid derivatives expressed by formula 1 by selective using of economically favorable catalyst which results in superior reaction rate and yield.

What is claimed is:

1. A preparing method of 2-phenylalkanoic acid derivatives expressed by formula 1 from 5,6dihydro-2(4H)-benzofuranone expressed by formula 2 in the presence of a catalyst, characterized in that the catalyst is organic acid alkali metal salt,

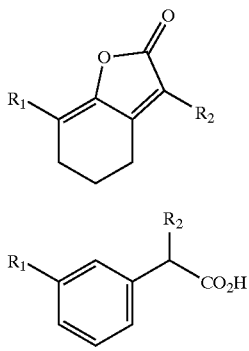

wherein $R_1$ represents benzoyl, naphthoyl, nicotinoyl, furoyl or thenoyl group; and $R_2$ represents a hydrogen atom or $C_1 \sim C_6$ alkyl group.

2. The preparing method of 2-phenylalkanoic acid derivatives according to claim 1, wherein the said organic acid alkali metal salt is used in the range of 0.01~5 molar equivalents to the starting material.

3. The preparing method of 2-phenylalkanoic acid derivatives according to claim 1, wherein the said organic acid alkali metal salt is used alone or as a mixture selected from salts of 2-phenylalkanoic acid derivatives expressed by formula 1 and salts expressed by formula 3 and salts which can convert to ones expressed by formula 3 in reaction solution, $$R\text{---}CO_2^-M^+ \quad (3)$$

wherein R represents a hydrogen atom, $C_1 \sim C_{13}$ alkyl, $C_1 \sim C_{13}$ haloalkyl, $C_1 \sim C_{13}$ alkenyl, $C_1 \sim C_{13}$ alkinyl, $C_1 \sim C_{13}$ alkoxyalkyl, $C_1 \sim C_{13}$ cycloalkyl, or $A\text{---}(CH_2)_n$, wherein A is aryl which is phenyl, naphthyl, pyridyl, quinolyl and thiophenyl, the aryl having more than one of the group consisting of a hydrogen atom and functional groups halogen atom, $C_1 \sim C_3$ alkyl, $C_1 \sim C_3$ alkoxy and nitro group, and n is 0 or an integer of 1~4; and M represents an alkali metal atom. An alkyl group of the present invention includes straight or branched alkyl group.

4. The preparing method of 2-phenylalkanoic acid derivatives according to claim 3, wherein the said organic acid alkali metal salt is organic acid potassium salt or organic acid sodium salt.

5. The preparing method of 2-phenylalkanoic acid derivatives according to claim 1, wherein the reaction is performed in the temperature range of 150~250° C.

6. The preparing method of 2-phenylalkanoic acid derivatives according to claim, 1, wherein the compound expressed by formula 1 is 2-(3-benzoylphenyl)-propionic acid.

* * * * *